United States Patent
Hess

(10) Patent No.: US 9,345,889 B2
(45) Date of Patent: May 24, 2016

(54) PATIENT SPECIFIC DATA DRIVEN SAFETY INTERLOCKS FOR MEDICAL DEVICES

(71) Applicant: Medtronic, Inc., Minneapolis, MN (US)

(72) Inventor: Michael F. Hess, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/341,227

(22) Filed: Jul. 25, 2014

(65) Prior Publication Data

US 2016/0023001 A1    Jan. 28, 2016

(51) Int. Cl.
| | |
|---|---|
| A61N 1/37 | (2006.01) |
| A61B 5/02 | (2006.01) |
| A61N 1/08 | (2006.01) |
| A61N 1/36 | (2006.01) |
| A61N 1/365 | (2006.01) |
| A61N 1/372 | (2006.01) |

(52) U.S. Cl.
CPC .............. *A61N 1/3706* (2013.01); *A61B 5/02* (2013.01); *A61N 1/08* (2013.01); *A61N 1/365* (2013.01); *A61N 1/36142* (2013.01); *A61N 1/37235* (2013.01)

(58) Field of Classification Search
None
See application file for complete search history.

(56) References Cited

U.S. PATENT DOCUMENTS

| | | | | |
|---|---|---|---|---|
| 6,058,326 | A  * | 5/2000 | Hess | A61N 1/3622 607/9 |
| 6,553,263 | B1 * | 4/2003 | Meadows | A61N 1/36071 607/33 |
| 6,961,448 | B2 | 11/2005 | Nichols et al. | |
| 7,096,064 | B2 * | 8/2006 | Deno | A61N 1/36114 607/9 |
| 7,460,910 | B2 * | 12/2008 | Webb | A61N 1/37282 607/30 |
| 7,565,197 | B2 * | 7/2009 | Haubrich | G06F 19/3418 607/30 |

(Continued)

OTHER PUBLICATIONS (PCT/US2015/035029) PCT Notification of Transmittal of the International Search Report and the Written Opinion of the International Searching Authority, Mailed Sep. 3, 2015, 10 pages.

*Primary Examiner* — Brian T Gedeon

(57) ABSTRACT

A medical device is provided that includes an input/output, at least one sensor, a memory, a controller and at least one delivery member. The input/output is configured to provide a communication path to and from the medical device. The at least one sensor is used to monitor at least one patient function. The memory is used to store patient specific data from the at least one sensor and operating parameters of the medical device. The controller is used to control operations of the medical device. The controller is in communication with the at least one sensor, the memory and the input/output. The controller is configured to deny device operational change requests received via the input/output based at least in part on the patient specific data sensed by the at least one sensor. The at least one delivery member is under the control of the controller and is configured to provide a therapeutic function of the medical device.

20 Claims, 7 Drawing Sheets

(56) References Cited

U.S. PATENT DOCUMENTS

| | | | |
|---|---|---|---|
| 7,787,942 B2 | 8/2010 | Chinchoy et al. | |
| 7,840,268 B2 * | 11/2010 | Blischak | A61M 5/14276 607/30 |
| 7,983,755 B2 * | 7/2011 | Starkebaum | A61N 1/36007 607/40 |
| 8,140,160 B2 * | 3/2012 | Pless | A61N 1/36064 607/27 |
| 8,332,030 B2 | 12/2012 | Hess et al. | |
| 8,401,646 B2 | 3/2013 | Stadler et al. | |
| 8,518,021 B2 * | 8/2013 | Stewart | A61M 5/14228 604/500 |
| 8,634,926 B2 | 1/2014 | Hess et al. | |
| 8,639,340 B2 | 1/2014 | Sommer et al. | |
| 8,738,131 B2 | 5/2014 | Chinchoy et al. | |
| 8,918,174 B2 * | 12/2014 | Woods | A61N 1/36071 607/117 |
| 2001/0031986 A1 | 10/2001 | Hauck | |
| 2005/0283198 A1 | 12/2005 | Haubrich et al. | |
| 2010/0058462 A1 | 3/2010 | Chow | |
| 2010/0137945 A1 | 6/2010 | Gadagkar et al. | |
| 2012/0046711 A1 | 2/2012 | Osorio | |
| 2013/0150911 A1 | 6/2013 | Perschbacher et al. | |

* cited by examiner

PATIENT SPECIFIC DATA DRIVEN SAFETY INTERLOCKS FOR MEDICAL DEVICES

BACKGROUND

Medical devices, such as implantable medical devices, are used for delivering a therapy and/or monitoring physiological conditions of a patient. For example, an implantable medical device may deliver electrical stimulation or fluid therapy to, and/or monitor conditions associated with, the heart, muscle, nerve, brain, stomach or other organs or tissues of the patient. Example implantable medical devices include cardiac pacemakers, cardioverters, defibrillators and, devices that combine two or more functions of the aforementioned example implantable medical devices.

It is common for medical devices, such as implantable medical devices, to include a memory that stores parameters that define operations of the implantable medical device. A health care professional, based on measured patient functions, typically sets the operating parameters of the implantable medical device. The operating range of a medical device is typically very broad to accommodate a wide range of patients and their conditions. However parts of a programmable range may not be appropriate or safe for a specific patient. Setting the correct programmable operating parameters of the implantable medical device is critical in providing a desired therapeutic benefit. Moreover, setting the programmable parameters within this range but outside of what is desirable for a specific patient could cause serious harm and even death to the patient. Currently care professionals require extensive training and experience to safely and effectively operate the implantable medical device system. However the proliferation of medical device patients leads to a broader population of health care professionals interacting with the medical devices who may not have had the same extensive training.

For the reasons stated above and for other reasons stated below which will become apparent to those skilled in the art upon reading and understanding the present specification, there is a need in the art for an effective and efficient method of limiting programmable parameters of a implantable medical device based on patient specific data to provide personalized programmable ranges which are appropriate for a wide range of healthcare professionals.

SUMMARY OF INVENTION

The above-mentioned problems of current systems are addressed by embodiments of the present invention and will be understood by reading and studying the following specification. The following summary is made by way of example and not by way of limitation. It is merely provided to aid the reader in understanding some of the aspects of the invention.

In one embodiment, a method of generating patient specific interlocks for a medical device is provided. The method includes sensing at least one patient function of a patient with a medical device. Sensed patient function data is then collected from the sensing of the at least one patient function. The collected patient function data is then analyzing. Based at least in part on the analyzed collected patient function data, at least one patient specific interlock is generated that denies specific operational change requests to the medical device.

In another embodiment, a method of operating a medical device is provided. The method includes measuring at least one patient function with the medical device. When a request to change at least one operating parameter of a medical device is received at an input to the medical device, applying at least one patient specific interlock, that is based at least in part on the at least one measured patient function, to determine if the requested change to the at least one operating parameter of the medical device should be permitted. Requests to change the at least one operating parameter of the medical device are denied when it is determined the at least one patient specific interlock does not allow the requested change.

In further another embodiment, a medical device is provided. The medical device includes an input/output, at least one sensor, a memory, a controller and at least one delivery member. The input/output is configured to provide a communication path to and from the medical device. The at least one sensor is used to monitor at least one patient function. The memory is used to store patient specific data from the at least one sensor and operating parameters of the medical device. The controller is used to control operations of the medical device. The controller is in communication with the at least one sensor, the memory and the input/output. The controller is configured to deny device operational change requests received via the input/output based at least in part on the patient specific data sensed by the at least one sensor. The at least one delivery member is under the control of the controller and is configured to provide a therapeutic function of the medical device.

BRIEF DESCRIPTION OF THE DRAWINGS

The present invention can be more easily understood and further advantages and uses thereof will be more readily apparent, when considered in view of the detailed description and the following figures in which.

In accordance with common practice, the various described features are not drawn to scale but are drawn to emphasize specific features relevant to the present invention. Reference characters denote like elements throughout Figures and text.

DETAILED DESCRIPTION

In the following detailed description, reference is made to the accompanying drawings, which form a part hereof, and in which is shown by way of illustration specific embodiments in which the inventions may be practiced. These embodiments are described in sufficient detail to enable those skilled in the art to practice the invention, and it is to be understood that other embodiments may be utilized and that changes may be made without departing from the spirit and scope of the present invention. The following detailed description is, therefore, not to be taken in a limiting sense, and the scope of the present invention is defined only by the claims and equivalents thereof.

Figure 1:
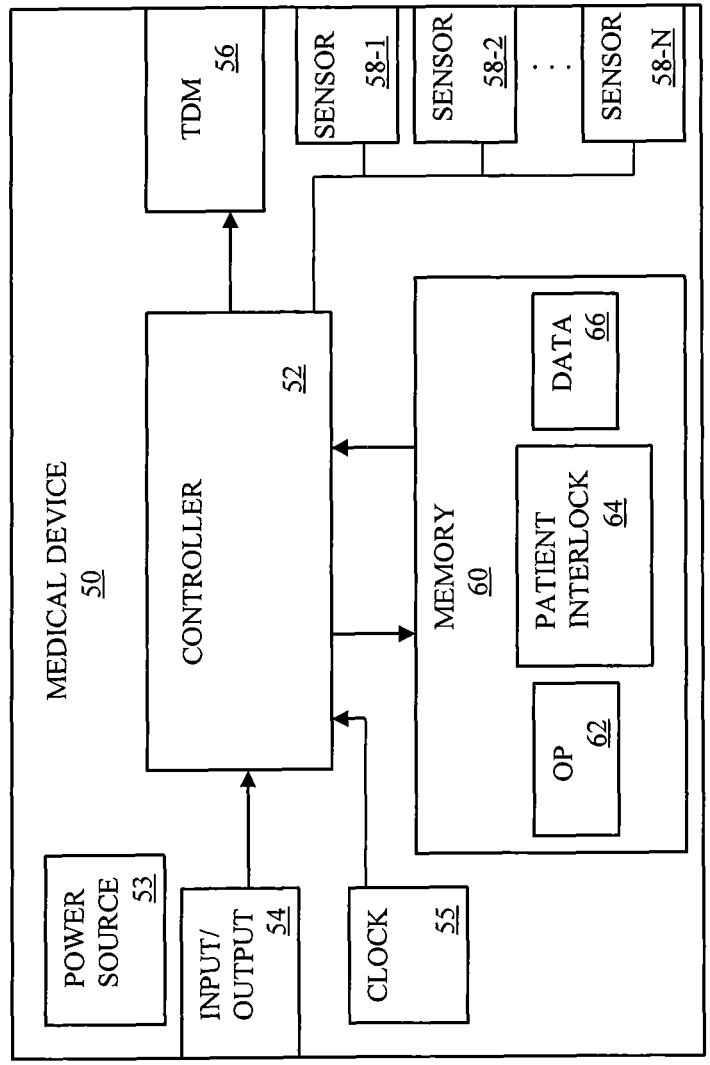
FIG. 1 is a block diagram of a medical device of an embodiment of the present invention.

In embodiments, clinical data collected by a medical device is used at least in part to create patient specific interlocks for the medical device. The patient specific interlocks prevent the medical device from performing operation functions that could harm the patient. In particular, the patient specific interlocks are used to deny requests to change operation parameter functions to protect the patient. Referring to FIG. 1, a block diagram of a medical device 50 of an embodiment is illustrated. The medical device can be any type of device designed to provide a therapeutic treatment. Example medical devices include implantable medical devices (IMD) that may deliver electrical stimulation or fluid therapy. The medical device 50 includes a controller 52 (or processor) that controls the operation of the device 50. The controller 52 is in communication with an input/output 54. The input/output 54 provides a communication path between an outside user, such as medical technician, doctor, programmer, etc. and the controller 52 of the medical device 50. For example the input/output 54 may provide an instruction path regarding operation of the medical device 50 and patient specific data output. In an embodiment where the medical device is an IMD, the input/output 54 may include a transceiver that is used to send and receive information wirelessly. Also illustrated in the block diagram of the medical device is a therapeutic delivery member 56 (TDM). The therapeutic delivery member 56 provides the function (therapeutic function) of the medical device 50 to the patient. The controller 52 controls the TDM 56. Sensors 58-1 through 58-N are used to monitor functions of the patient. The controller 52 is in communication to receive signals from sensors 58-1 through 58-N. Also included in this example medical device 50 is a memory 60. The memory 60 is used to store instructions and data. In this example embodiment, the memory 60 includes operating parameter instructions 62 which the controller 52 uses to control the delivery member 56 of medical device 50. As stated above, the memory also includes data 66 collected by the sensors 58-1 through 58-N and patient specific interlocks 64. The patient specific interlocks are set by the controller based at least in part on the sensor data. Example patient specific interlocks 64 are described further in detail below. Also illustrated in the embodiment of FIG. 1 is a power source 53 (such as a battery). The power source 53 is coupled to provide power to the elements of the medical device. Further, a clock 55 is used by the controller 52 for process timing.

The controller 52 (processor) may include any one or more of a microprocessor, a digital signal processor (DSP), application specific integrated circuit (ASIC), a field program gate array (FPGA), or equivalent discrete or integrated logic circuitry. In some example embodiments, controller 52 may include multiple components, such as any combination of one or more microprocessors, one or more controllers, one or more DSPs, one or more ASICs, one or more FPGAs, as well as other discrete or integrated logic circuitry. The functions attributed to controller 52 herein may be embodied as software, firmware, hardware or any combination thereof. Memory 60 may include computer-readable instructions that, when executed by controller 52 provide functions of the medical device 50. The computer readable instructions may be encoded within the memory 60. Memory 60 may comprise computer readable storage media including any volatile, non-volatile, magnetic, optical, or electrical media, such as, but not limited to, a random access memory (RAM), read-only memory (ROM), non-volatile RAM (NVRAM), electrically-erasable programmable ROM (EEPROM), flash memory, or any other type of storage media.

Figure 2:
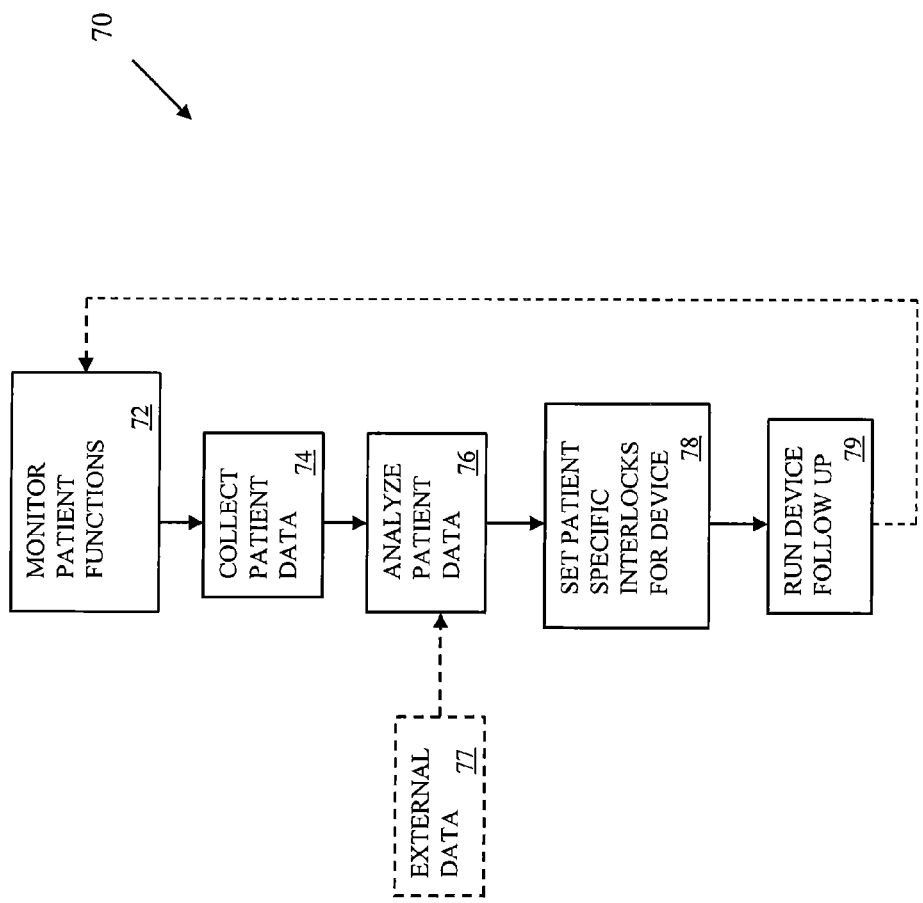
FIG. 2 is a device setup flow diagram of one embodiment of one embodiment of the present invention.

Referring to FIG. 2, a device setup flow diagram 70 of one embodiment is illustrated. The process starts by monitoring patient functions with the sensors 58-1 through 58-N (72). Data from the sensors 58-1 though 58-N are collected and stored in the memory 60 (74). Once, enough data points are collected, the controller 52 analyzes the collected patient data (76). Based at least in part on the analyzed data, patient specific interlocks are set for the device (78). The patient specific interlocks are used, as discussed above, to limit operating parameter change requests to the medical device 50 based on the patient's then current condition. In this embodiment, the type of implantable medical device requires a routine in-clinic evaluation to ensure proper device function. During this follow-up, the healthcare professional has the opportunity to evaluate device settings and change operating paramters. At the start of this embodiment, a device follow up is then run (79). The process then continues at step (72) where the patient function is monitored. Hence, in this example embodiment, the patient specific interlocks are dynamically defined as the patient data is collected from the IMD. In one embodiment, not only is the collected data analyzed, external data relating to the patient is provided (77) through the input/output 54. Hence, in this embodiment both measured patient data from the medical device 50 and external patient data is used at least in part to set the specific patient interlocks of the device at that point in time. A follow-up on the same patient at a different time with different patient data from the medical device or external data could result in different patient interlocks.

Figure 3:
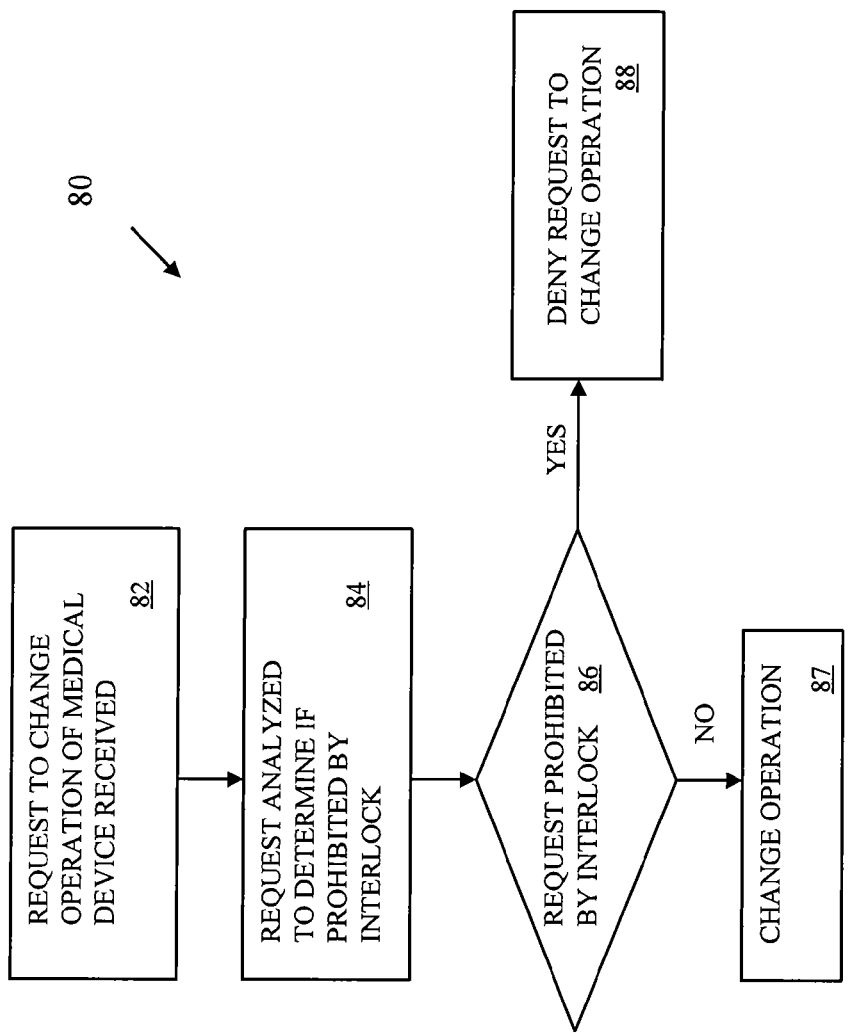
FIG. 3 is an application flow diagram of one embodiment of the present invention.

FIG. 3 illustrates an application flow diagram 80 of an embodiment. As illustrated, the process starts when a request to change the operation of the medical device is received (82). The request would typically come via way of the input/output 54 of the medical device 50 from a medical technician, doctor, programmer, etc. The request is analyzed by the controller 52 to determine if it is prohibited by any of the patient specific interlocks of the device 50 (84). If the request is not prohibited by the patient specific interlock (86), the controller changes operation of the medical device 50 according to the request (87). However, if the request is prohibited by the patient specific interlock, the request to change the operation of the medical device 50 is denied (88). Alternatively the programmable range of the parameter to be changed will have been limited by the system based on the analysis of patient data so the operator will only be able to make changes within the allowed range. Hence, the patient specific interlock system provides a built in safety for the medical devices so that attempts to change the operation of the device that could potentially harm a patient, because of the current condition patient, are denied or prevented from being requested.

Figure 4:
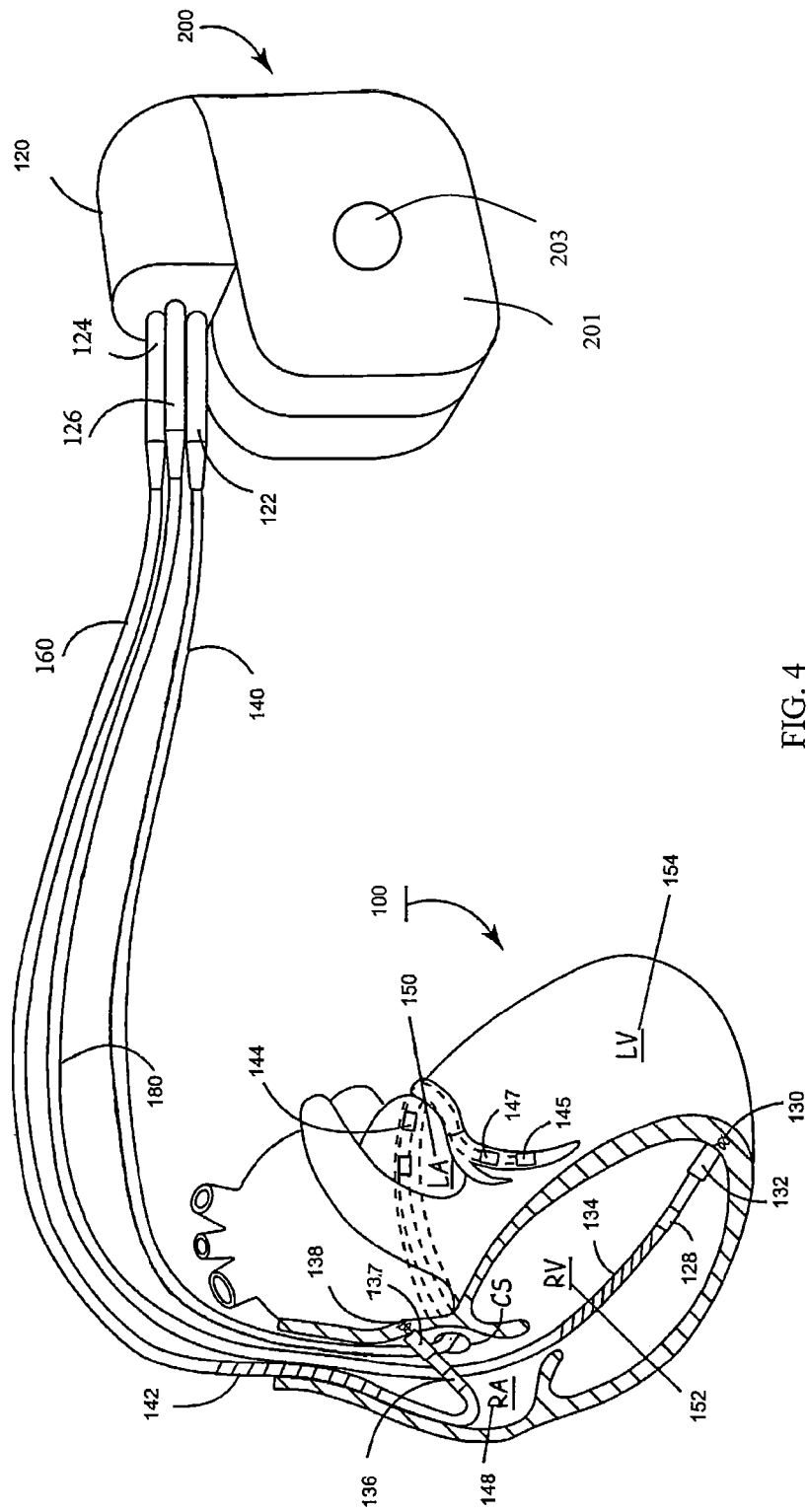
FIG. 4 is a drawing of a patient heart with an implantable medical device attached, the implantable medical device having patient specific data driven interlocks of one embodiment of the present invention.

An example IMD 200 that can use a patient specific interlock is illustrated in FIG. 4. The example IMD 200 in FIG. 4 is a cardiac device that monitors and delivers therapy to a heart 100. The heart 100 is shown having a right ventricle 152 (RV), left ventricle 154 (LV), right atrium 148 (RA) and left atrium 150 (LA). IMD 200 may provide pacemaker, cardioverter and/or defibrillator therapy for the heart 100. The implantable medical device 200 in this example embodiment is coupled to the heart 100 by way of a coronary sinus lead 140, a right atrial lead 160, and a right ventricular lead 180. IMD 200 includes a connector block 120 that receives connectors 122, 124 and 126 positioned on the proximal ends of the respective coronary sinus lead 140, right atrial lead 160 and right ventricular lead 180. Connectors 122, 124 and 126 provide electrical connectivity between leads 140, 160, 180 and electronic circuitry (shown in FIG. 5) within implantable medical device 200.

In the example of FIG. 4, a ring electrode 128, an extendable helix electrode 130 that is mounted retractably within an electrode head 132 and a coil electrode 134 are positioned on right ventricular lead 180. The ring electrode 128, the extendable helix electrode 130 and the coil electrode 134 are electrically coupled to an insulated conductor within right ventricular lead 180. As illustrated, right ventricular lead 180 is positioned such that its distal end is in the RV 152 for sensing right ventricular cardiac signals and delivering pacing or shocking pulses in the RV 152. The proximal end of the insulated conductors are coupled to corresponding connectors carried by bifurcated connector 126 for providing electrical connection to implantable medical device 200.

Right atrial lead 160 in this example, includes a ring electrode 136 and extendable helix electrode 138 that is mounted retractably within electrode head 137 for sensing and pacing in the RA 148. Right atrial lead 160, in this example, includes coil electrode 142 to deliver high-energy shock therapy. Right atrial lead 160 is positioned such that its distal end is in the vicinity of the RA 148 and the superior vena cava. Ring electrode 136, helix electrode 138 and coil electrode 142, in this example, are connected to an insulated conductor within the body of right atrial lead 160. The insulated conductor is coupled at its proximal end to bi-furcated connector 124 as shown.

Coronary sinus lead 140, in this example, includes defibrillation coil electrode 144 that may be used in combination with coil electrode 134 or coil electrode 142 for delivering electrical shocks for cardioversion and defibrillation therapies. Coronary sinus lead 140 may be advanced within the vasculature of the left side of heart 100 via the coronary sinus (CS) and great cardiac vein. In various embodiments, coronary sinus lead 140 may also include a distal tip electrode 145 and ring electrode 147 for pacing and sensing functions in the left chambers of the heart. Coil electrode 144 is coupled to an insulated conductor within the body of lead 140. The insulated conductor is coupled at its proximal end to connector 122.

Electrodes 128, 130, 136 and 138 may be used to form bipolar pairs. Various ones of such bipolar pairs may be referred to as "tip-to-ring" pairs. Electrodes 128, 130, 136 and 138 may likewise be utilized individually in unipolar configuration with implantable medical device housing 146 serving as an indifferent electrode, commonly referred to as the "can" or "case" electrode. A housing 201 of the IMD 200 in the example embodiment of FIG. 4 includes an electrode 203. Electrode 203 serves as a subcutaneous defibrillation electrode in combination with one or more of coil electrodes 134, 142 and 144 for defibrillation of atria or ventricles of heart 100. In various embodiments, alternate lead systems may be substituted for the lead system of the example embodiment of FIG. 4. Moreover, leads for use with a single chamber, dual chamber, or multichamber implantable medical devices may be utilized. The IMD 200 may deliver pacing pulses via any bipolar or unipolar combination of electrodes 128, 130, 134, 136, 138, 142, 144, 145 and 147. The IMD may also deliver cardioversion or defibrillation pulses to the heart 100 via combination of electrodes 128, 130, 134, 136, 138, 142, 144, 145 and 147.

Figure 5:
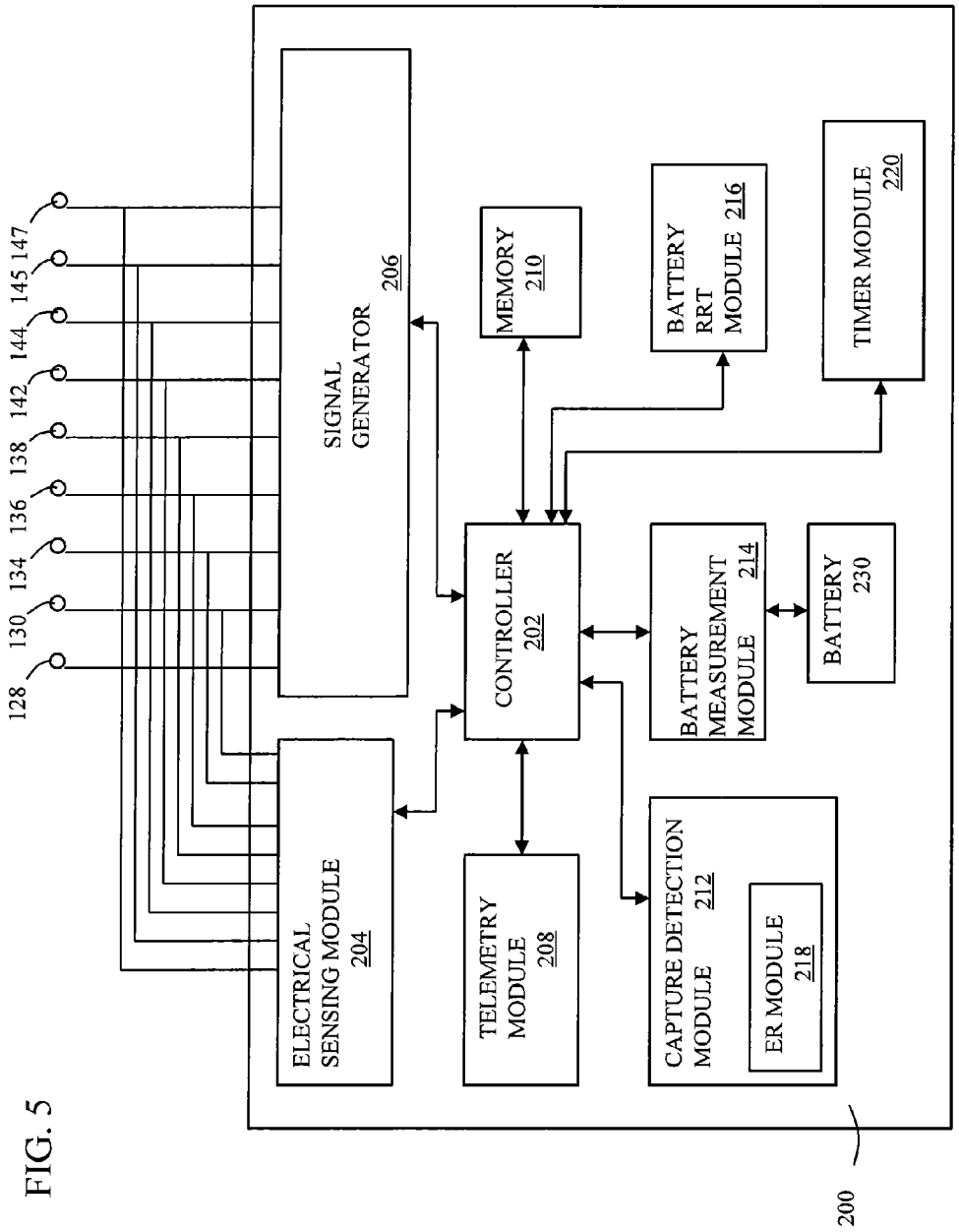
FIG. 5 is block diagram of the implantable medical device of FIG. 4.

Referring to FIG. 5, a block diagram illustrating an example configuration of IMD 200 of an embodiment is illustrated. In the example illustrated in FIG. 2, IMD 200 includes a controller 202, a memory 210, a signal generator 206, an electrical sensing module 204, a telemetry module 208, a capture detection module 212, a battery measurement module 214, a battery RRT module 216, a timer module 220 and a battery 230. Further in this example, the capture detection module 212 includes an evoked response detection module 218.

As discussed above, controller 202 controls signal generator 206 to deliver stimulation therapy, e. g., cardiac pacing or cardiac resynchronization therapy (CRT), to heart 100 according to a selected one or more therapy programs, which may be stored in memory 210. Signal generator 206 is electrically coupled to electrodes 128, 130, 134, 136, 138, 142, 144, 145 and 147 via conductors of the respective leads 140, 160, and 180. The signal generator 206 may include a switch module (not shown) to select via data/address bus, which of the available electrodes 128, 130, 134, 136, 138, 142, 144, 145 and 147 are used to deliver pulses, such as pacing pulses and stimulus pulses. The electrical sensing module 204 monitors signals from at least one of electrodes (sensors) 128, 130, 134, 136, 138, 142, 144, 145 and 147 in order to monitor patient functions (which is the electrical activity of the heart 100 in this embodiment). The electrical sensing module 204 may also include a switch module (not shown) to select which of the available electrodes 128, 130, 134, 136, 138, 142, 144, 145 and 147 are used to sense the cardiac activity.

Memory 210 includes computer-readable instructions that, when executed by controller 202, provide functions of the implantable medical device 200. Such functions include the functions of the capture detection module 212, the battery measurement module 214, the signal generator 206, the telemetry module 208 and the battery RRT module 216. The computer readable instructions may be encoded within the memory 210. Moreover, memory 210 stores intervals, counters, or other data used by the controller 202 to control the delivery of pacing pulses by signal generator 206. Such data may include, but is not limited to, intervals and counters used by controller 202 to control the delivery of pacing pulses to one or both of the left and right ventricles for CRT. The intervals and/or counters are, in some examples, used by controller 202 to control the timing and delivery of pacing pulses relative to an intrinsic or paced event, e. g., in another chamber. One function of the capture detection module 212 is detecting capture and loss of capture (LOC) during capture detection tests. Capture detection module 212 uses timer module 220 to determine when to deliver pacing pulses and to determine conduction times between chambers of the heart. The capture detection module 212 uses the evoke response detection module 218 for detecting the amplitude and timing of an evoked response which may be used additionally or alternatively for detecting capture or LOC.

Battery 230 provides power to operate each of the electrical components of the IMD 200. The components may include the controller 202, the memory 210, the signal generator 206, the electrical sensing module 204, the telemetry module 208, the timer module 220 and the capture detection module 212. With some IMDs it is necessary to provide an indication that the battery should be replaced prior to battery depletion and the loss of function of the IMD. The RRT Module 216 provides this function.

Figure 6:
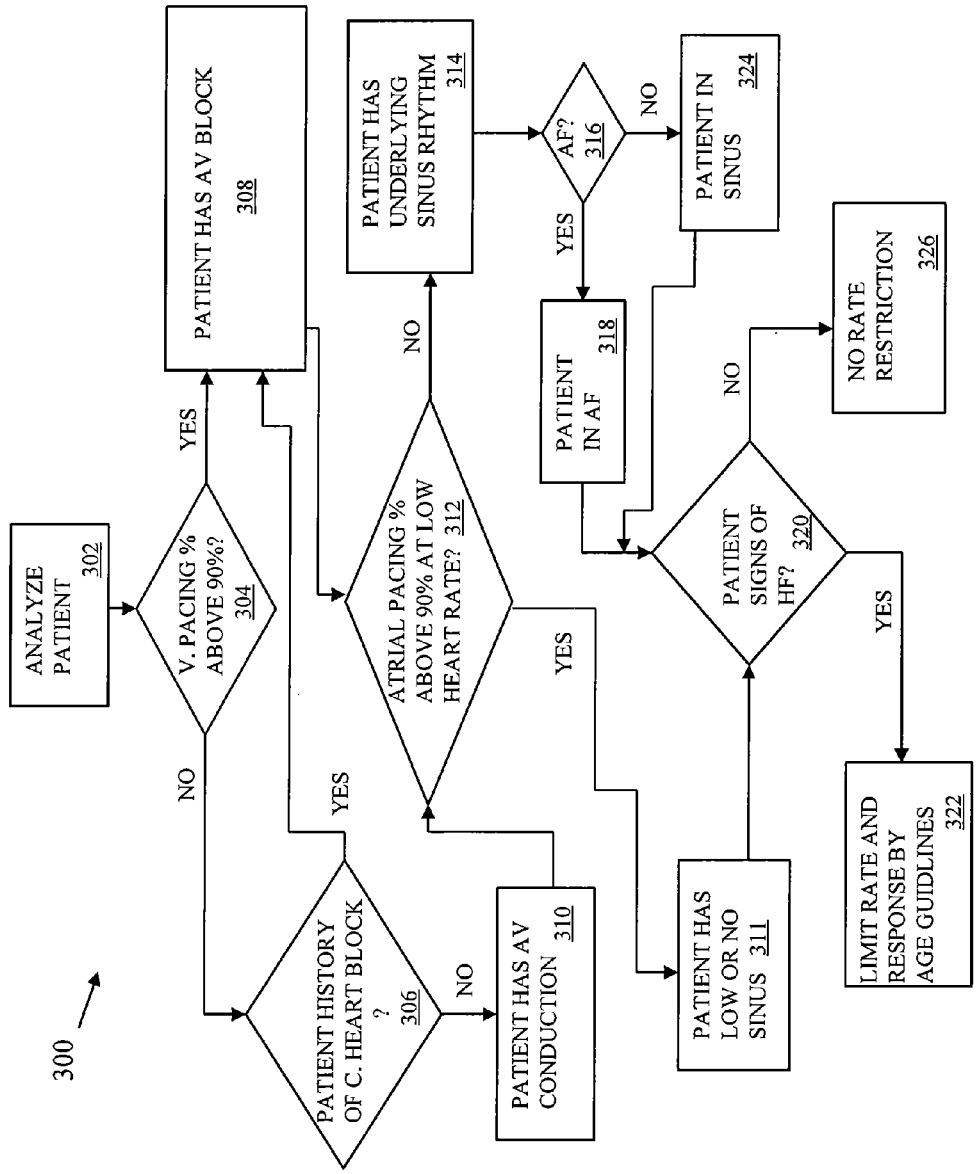
FIG. 6 is a patient specific interlock flow setup diagram of one embodiment of the present invention.

Referring to FIG. 6, a patient specific interlock flow setup diagram 300 is illustrated for an IMD such as IMD 200 described above is provided. The process in this example embodiment starts by analyzing the patient (302). In an embodiment, this is done by the electrical sensing module 204 monitoring signals from at least one of electrodes (sensors) 128, 130, 134, 136, 138, 142, 144, 145 and 147 in order to monitor electrical activity of the heart 100. From the data received from the electrical sensing module 204, the controller 202, in this embodiment, determines if the ventricular pacing percent is above 90% (304). If the ventricular pacing percent is not above 90% (304), it is then determined if the patient has a history of complete heart block (306). This prior patient history, in one embodiment, is communicated to the controller 202 via the telemetry module 208 (which provides an input/output communication passage for the controller 202). If the patient does not have a history of complete heart block (306), it is determined if the patient has an atrioventricular conduction (310). If this is the case, it is then determined if the atrial pacing percent is above 90% at a low heart rate (312). If the atrial pacing percent is not above 90% at a low heart rate (312), the patient has an underlying sinus rhythm (314). If this is the case, it is then determined if the patient is in atrial fibrillation (316). If the patient is not in atrial fibrillation (316), the patient is in sinus (324). If the patient is in sinus (324), it is then determined if the patient data shows signs of heart failure (320). If the patient data does not show signs of heart failure (320), no rate restriction is required (326). Hence, a patient specific interlock will not be created in this scenario to block rate restriction requests to the IMD. If there was a sign of heart failure at step (320), a patient specific interlock with a limit rate and response by age guidelines is created and implemented (322). Thereafter requests to the IMD 200 beyond the set limit rate and response will be denied by the patient specific interlock.

If at step (316) it was determined the patient was in atrial fibrillation, the patient is designated as being in atrial fibrillation (318). It is then determined if the patient shows signs of heart failure (320). If the patient shows signs of heart failure (320), a patient specific interlock with a limit rate and response by age guidelines is created and implemented (322). Otherwise, the patient specific interlock will not place a rate restriction requests on the IMD (326). Further in this example embodiment, if it was determined that the atrial pacing percent was above 90% at a low heart rate at step (312), it is determined the patient has low or no sinus (311). If this is the case, it is then determined if the patient shows signs of heart failure (320). If the patient shows signs of heart failure at step (320), a patient specific interlock with a limit rate and response by age guidelines is created and implemented (322). Otherwise, a patient specific interlock will not be created to limit rate restriction requests on the IMD (326). Moreover, if the patient history includes a coronary heart block at step (306), the patient is designated as having an atrioventricular block (308). If this is the case, it is determined if the atrial pacing percent is above 90% at a low heart rate at step (312) and the process continues as described above. Moreover, if it is determined, in this embodiment, that the ventricular pacing percent is above 90% at step (304), it is determined the patient has an atrioventricular block (308). If the patient has an atrioventricular block (308), it is then determined if the atrial pacing percent is above 90% at a low heart rate at step (312) and the process continues as described above.

Figure 7:
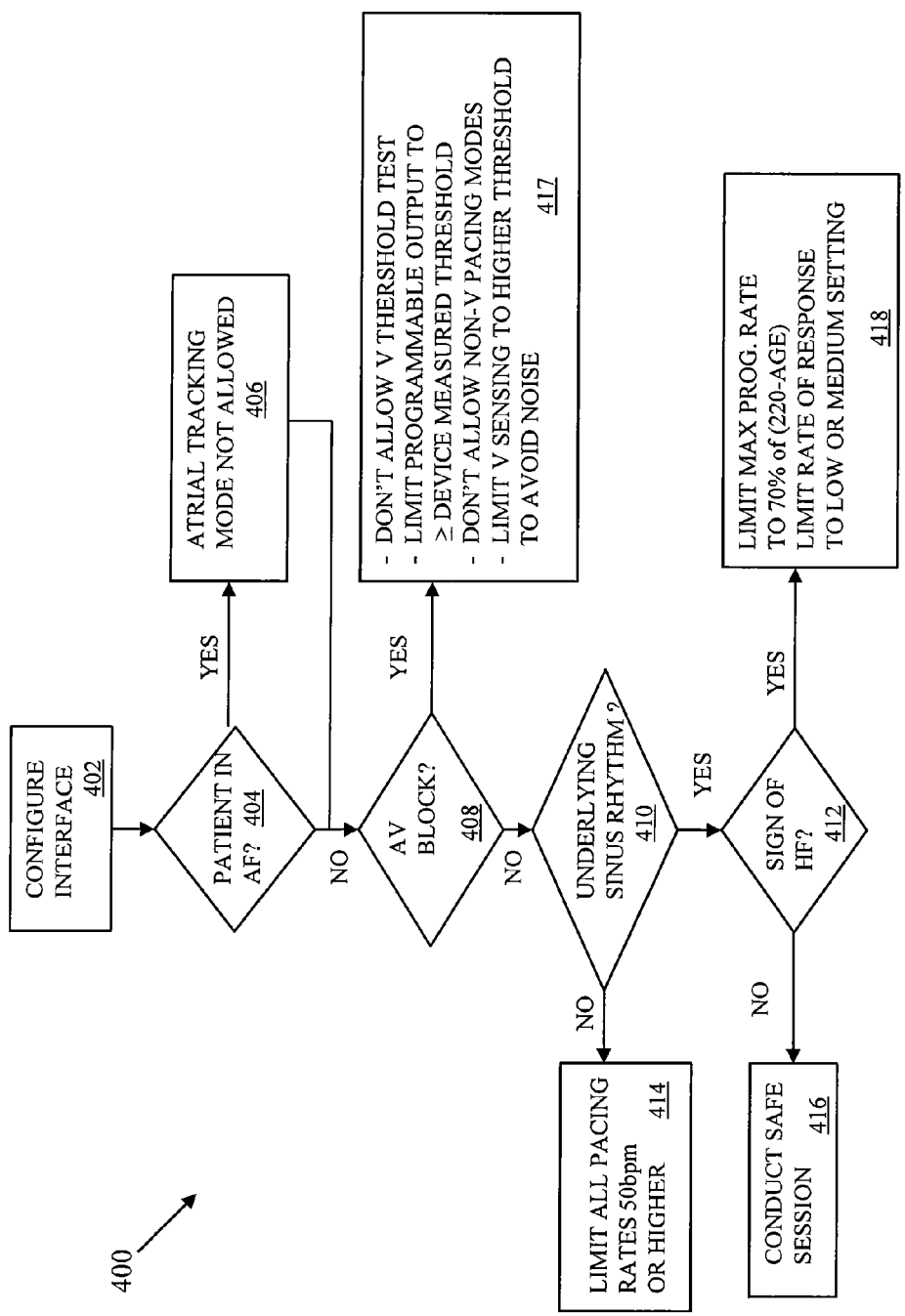
FIG. 7 is a patient specific interlock implementation flow diagram of another embodiment of the present invention.

An example patient specific interlock implementation flow diagram 400 is illustrated in FIG. 7. In this example embodiment, an interface is first configured (402). The interface, in this embodiment is between a care professional and the IMD and is based on determinations of patient specific interlocks, such as those determined in the patient specific interlock flow setup diagram 300 example discussed above. Once the interface is configured (402), it is determined if the patient is in atrial fibrillation (404). If the patient is in atrial fibrillation (404), a specific patient interlock is set so an atrial tracking mode will not be allowed (406). Further in this example embodiment, if the patient is determined not to be in atrial fibrillation (404), the process continues by determining if the patient has an atrioventricular block (408). If it determined that the patient has an atrioventricular block (408), a patient specific interlock is set to at least one of the following: not allow a ventricular pacing threshold test; limit programmable output to device measured threshold; not allow non-ventricular pacing modes; and limit ventricular sensing threshold settings to higher threshold to avoid noise (417). If it is determined that the patient does not have atrioventricular block (408), it is then determined if the patient has an underlying sinus rhythm (410). If the patient does not have an underlying sinus rhythm (410), a patient specific interlock is set to limit all pacing rates to 50 bpm or higher (414). If the patient has an underlying sinus rhythm (410), it is determined if the patient shows signs of heart failure (412). If the patient does not show signs of heart failure (412), a patient specific interlock is not set and the device allows a safe session to be conducted (416). If, however, the patient does show signs of heart failure (412), a patient specific interlock is set to limit a maximum programmable rate to 70% of (220-age) limit rate of response to low or medium setting (418). In all of the above cases specific percentages such as 90% or 70% are illustrative and may be changed for different implementations of the system.

As described above in the example embodiments, the use of clinical data collected by the medical device is used to set patient specific interlocks that limit functional ranges for a specific patient device. Other types of patient specific interlocks for cardiac devices are contemplated based on specific patient data. For example, in an embodiment, a percentage of pacing that occurs for a patient may lead to patient specific interlocks that do not permit a permanent inhibited pacing mode (OVO, ODO). The interlock in this embodiment may also be set to restrict a lower rate request. For example, a normal range of 30 bpm would typically be available, however, in this patient a patient specific interlock may set the lowest rate at 50 bpm. In another embodiment where the cardiac device is capable of making output measurements to track pacing thresholds, a patient specific interlock is set to not allow permanent output setting requests that could lose capture. In yet another embodiment the interlock restricts output to super-threshold values which could excessively deplete the battery with no benefit to the patient. In still another example embodiment, only in-clinic execution of a safe controlled threshold test that automatically restores adequate pacing output is allowed by a patient specific interlock. Moreover in one embodiment a patient specific interlock is configured to only allow specific device operation change requests by specific personnel. Hence, in this embodiment the patient specific interlock is also unique to the person who is requesting the change in operation of the medical device.

Further in one embodiment, if the cardiac device determines the patient has progressed into permanent atrial fibrillation, or the patient is measured to be in atrial fibrillation at a clinic, a patient specific interlock of the cardiac device is set to prevent high rate symptomatic tracking of the arrhythmia to the ventricle. In another example embodiment, the patient specific interlock sets sensing thresholds to prevent under sensing which may lead to asynchronous pacing in cardiac devices that track amplitude of cardiac signals. Moreover, in another example embodiment a patient specific interlock limits pacing rates on the higher side to prevent prolonged fixed rate pacing at rates that could cause symptoms or lead to heart failure progression. The specific patient interlock in this embodiment is based on dynamic excursions measured during a patient's ambulatory life or clinical inputted age. In yet another example embodiment, the patient specific interlock prevents settings requests that unnecessarily impact device longevity, such as but not limited to, output amplitudes that greatly exceed measured thresholds.

Other examples of this invention can be envisioned where the therapy is not cardiac stimulation, for example neural stimulation or fluid/drug delivery, where the same method of evaluating patient specific physiologic data is used to configure the patient specific interface settings and allowable ranges and programming settings.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

The invention claimed is:

1. A method of generating patient specific interlocks for a medical device, the method comprising:
   sensing at least one patient function of a patient with a medical device;
   collecting sensed patient function data from the sensing of the at least one patient function;
   analyzing the collected patient function data; and
   based at least in part on the analyzed collected patient function data, generating at least one patient specific interlock that denies specific operational change requests to the medical device.

2. The method of claim 1 further comprising:
   dynamically changing the at least one patient specific interlock based on then current patient function data.

3. The method of claim 1, wherein generating the at least one patient specific interlock further comprises:
   using externally provided patient specific data along with the analyzed collected patient function data.

4. The method of claim 1, wherein generating the at least one patient specific interlock, further comprises:
   setting prohibited operating parameter requests for the medical device.

5. The method of claim 4, wherein the prohibited operating parameter requests further comprise at least one of prohibiting specific pacing rate requests, pacing mode requests, threshold test requests, rates of response requests, tracking modes requests, permanent output setting requests that lose capture, output to super-threshold value requests, requests that effect the longevity of the medical device and symptomatic tracking requests.

6. The method of claim 1, wherein measuring the at least one patient function of the patient with a medical device further comprises:
   measuring electrical activity of the patient's heart.

7. The method of claim 1, wherein the at least one patient specific interlock that denies specific operational change requests is created to be unique to at least one of who is requesting the operational change of the medical device and the location of the medical device when the request is received.

8. The method of claim 1 wherein analyzing data from the collected patient function data further comprises at least one of determining if the patient function data indicates a ventricular pacing percent that is above a select percentage, determining if the patient function data indicates an atrial pacing percent that is above a select percentage, determining if the patient function data indicates that the patient is in atrial fibrillation and determining if the patient function data indicates the patient is showing signs of heart failure.

9. A method of operating a medical device, the method comprising:
   measuring at least one patient function with the medical device;
   when a request is received at an input to the medical device to change at least one operating parameter of a medical device, applying at least one patient specific interlock that is based at least in part on the at least one measured patient function to determine if the requested change to the at least one operating parameter of the medical device should be permitted; and
   denying the input request to change the at least one operating parameter of the medical device when it is determined that the at least one patient specific interlock does not allow the requested change.

10. The method of claim 9, further comprising:
    generating the at least one patient specific interlock with patient specific data from the measured at least one patient function.

11. The method of claim 10, further comprising:
    generating at least some of the patient specific data from externally provided patient information; and
    using the external patient information at least in part to generate the patient specific interlock.

12. The method of claim 9, further comprising:
    dynamically changing the at least one patient specific interlock based on then current measured at least one patient function.

13. The method of claim 9, further comprising:
    analyzing patient specific data from the measured at least one patient function; and
    setting allowable parameters of the medical device based at least in part on the analyzed patient specific data.

14. The method of claim 9, wherein the at least one patient specific interlock prohibits at least one of specific pacing rate requests, pacing mode requests, threshold test requests, rates of response requests, tracking mode requests, permanent output setting requests that lose capture, output to super-threshold value requests, requests that effect the longevity of the medical device and symptomatic tracking requests.

15. A medical device comprising:
    an input/output configured to provide a communication path to and from the medical device;
    at least one sensor to monitor at least one patient function;
    a memory to store patient specific data from the at least one sensor and operating parameters of the medical device;
    a controller to control operations of the medical device, the controller in communication with the at least one sensor, the memory and the input/output, the controller configured to deny device operational change requests received via the input/output based at least in part on the patient specific data sensed by the at least one sensor; and
    at least one delivery member under the control of the controller configured to provide a therapeutic function of the medical device.

16. The medical device of claim 15, wherein the controller is further configured to create at least one patient specific interlock based at least in part on the patient specific data sensed by the at least one sensor, the at least one specific interlock used by the controller to deny the specific operational change requests.

17. The medical device of claim 16, wherein the controller is still further configured to create the at least one patient specific interlock based at least in part from external patient specific data received through the input/output.

18. The medical device of claim 15, wherein the controller is further configured to dynamically change the at least one patient specific interlock based on then current patient specific data.

19. The medical device of claim 15, wherein the medical device is a cardiac device and the at least one sensor is at least one electrode configured to measure cardiac electrical activity of a patient's heart.

20. The medical device of claim 19, wherein the device operational change requests the controller is configured to deny include at least one of specific pacing rate requests, pacing mode requests, threshold test requests, rates of response requests, tracking mode requests, permanent output setting requests that lose capture, output to super-threshold value requests, requests that effect the longevity of the medical device and symptomatic tracking requests.

* * * * *